United States Patent [19] [11] 4,065,359
Hurni [45] Dec. 27, 1977

[54] CELL REMOVING DEVICE
[75] Inventor: William M. Hurni, North Wales, Pa.
[73] Assignee: Merck & Co., Inc., Rahway, N.J.
[21] Appl. No.: 702,819
[22] Filed: July 6, 1976

Related U.S. Application Data

[63] Continuation of Ser. No. 573,712, May 1, 1975, abandoned.

[51] Int. Cl.² ............................ C12K 9/00; C12K 1/10
[52] U.S. Cl. ...................................... 195/127; 195/1.7; 15/236 R
[58] Field of Search .................. 195/127, 1.7; 128/304; 15/236 R

[56] References Cited
U.S. PATENT DOCUMENTS

| 289,550 | 12/1883 | Miles | 15/142 |
| 1,085,063 | 1/1914 | Prouty et al. | 15/236 R |
| 1,916,842 | 7/1933 | Lander | 15/236 R |
| 2,291,015 | 7/1942 | Anderson | 15/236 R |
| 3,540,700 | 11/1970 | Freeman | 195/127 |
| 4,004,981 | 1/1977 | Hurni et al. | 195/127 |

OTHER PUBLICATIONS

Parker, Methods of Tissue Culture, Harper & Row Pub., pp. 187–188 (1961).

Primary Examiner—Alvin E. Tanenholtz
Attorney, Agent, or Firm—Donald J. Perrella

[57] ABSTRACT

Apparatus for physically removing cells in a sterile manner from a disc stack on which the cells have been cultured comprises a substantially shaft-like member having at least one butressed rod-like member mounted at substantially a right angle to the axis of the rod.

13 Claims, 5 Drawing Figures

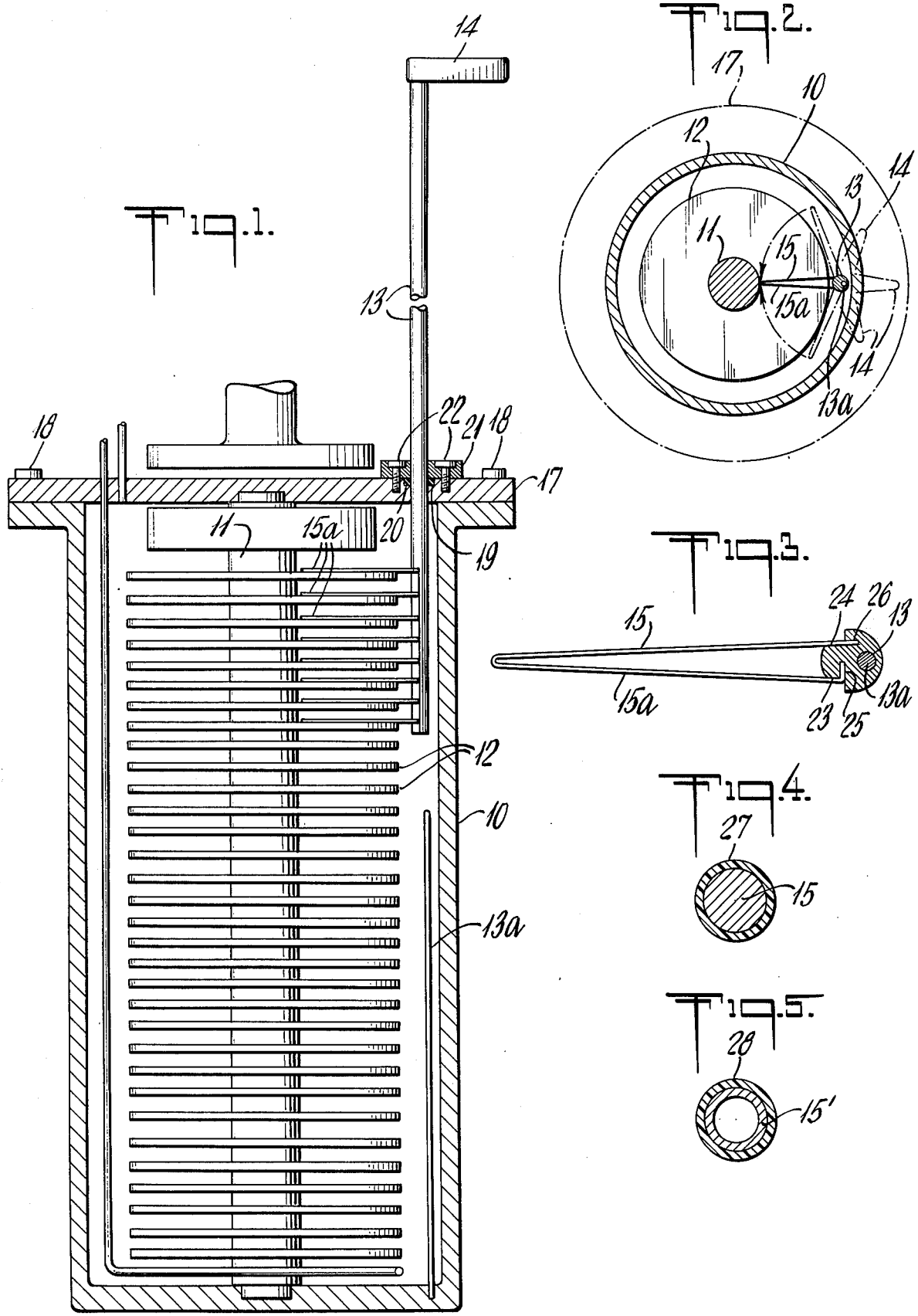

CELL REMOVING DEVICE

This is a continuation of application Ser. No. 573,712 filed May 1975 and now abandoned.

BACKGROUND OF THE INVENTION

The present invention relates to apparatus for removing cells and, more particularly, to apparatus for physically removing cells in sterile manner from a disc stack on which cells are cultured in a mass cell culture apparatus.

Systems have been developed for the mass culture of cells such as, for example, the multi-plate system disclosed in U.S. Pat. No. 3,407,120 and the Biotech cylindrical rotating disc apparatus. A major difficulty associated with the use of such mass culture systems, however, is that of removing the cells from the discs on which they have been cultured. Prior art method of removing the cells involve the use of enzymes, such as trypsin which have the disadvantage of causing, to some extent at least, undesired chemical degradation of the cells.

It is, accordingly, an object of the present invention to provide apparatus and method for physically removing cells in a sterile manner from discs on which they have been cultured. Another object of the present invention is to provide an apparatus and method for physically removing cells in sterile manner from the discs of the multi-plate or multi-disc mass cell culture apparatus. These and other objects will be apparent from the following detailed description.

SUMMARY OF THE INVENTION

Apparatus for sterily removing cells from a disc stack on which the cells have been cultured comprises a substantially rod-like member having at least one elongated member mounted at substantially a right angle to the axis of the rod. The elongated member may be provided with a flexible coating or may be surrounded with a flexible member.

BRIEF DESCRIPTION OF THE DRAWINGS

FIG. 1 is a sectional view of a multi-plate cell culture apparatus fitted with a cell removing device of the present invention;

FIG. 2 is a plan view of the apparatus of FIG. 1;

FIG. 3 is a plan view of a buttressed rod-like member;

FIGS. 4-5 are sectional views of various rod-like members.

DETAILED DESCRIPTION

Referring now to the drawings, FIG. 1 is a sectional view of a known rotating disc apparatus described in U.S. Pat. No. 3,839,155 whose disclosure is hereby incorporated by reference. The apparatus is equipped with a cell removing device according to the present invention preferably formed of a metal suitable for cell culture conditions, e.g., stainless steel or titanium. The apparatus comprises a cylindrical shell 10 having a central shaft 11 on which are mounted a plurality of discs 12 on whose surfaces the cells are cultured. Also, fixedly mounted on the shaft is a magnetic couple (not shown) which is engaged by external magnetic drive means (not shown) in order to rotate the discs 12. The cell removing device consists of a substantially shaft-like member 13 having a turning handle 14 at its uppermost end and a plurality of buttressed rod-like members 15, each of which is attached at about a right angle to a portion of the shaft. The shaft is of such length that member 15 which is furthest from the handle can contact the disc 12 which is furthest from the handle. Members 15 are spaced apart from one another so as to fit between remaining discs, to contact the lower surface of a disc closer to the handle and the upper surface of the adjacent disc furthest from the handle. The shaft 13 passes through a circular opening 16 in the cover plate 17 which is secured to the top of the apparatus by bolts 18. The shaft 13 is hollow and thereby adapted to fit over guide rod 13a which is fixed to bottom plate of shell.

A recessed flange 19 in the upper surface of opening 16 is adapted to receive and O-ring 20 which is covered with a cap 21 which is fixed to plage 17 by screws 22 to seal the opening 16.

FIG. 2 is a plan view of the rotating disc apparatus with plate 17 removed and showing cylindrical shell 10, central shaft 11 and top disc 12, turning handle 14 and the top rod-like member 15 with its buttressing member 15a. By turning handle 14, shaft 13 is rotated thereby sweeping buttressing member 15a and rod-like member 15 across the surface of disc 12 and displacing cells from the surface of disc 12 into the liquid medium in the apparatus from which liquid medium and cells suspended therein are drawn off. Alternatively, shaft 13 may be turned to engage members 15 and discs 12 and shaft 11 rotated to turn discs 12.

As shown in FIG. 3, the lower portion of shaft 13 has two flat surfaces 23 and 24 each provided respectively, with a recess 25, and 26. Recess 26 is adapted to receive the end of rod-like member 15 while recess 25 is adapted to receive the end of buttressing member 15a. Preferably, members 15 and 15a are formed by bending a single strip of material. Recesses 25 and 26 are substantially at right angles to each other to provide secure mounting while at the same time permitting easy removal. The end of member 15a is bent to fit into recess 25. Member 15 may be provided with a coating or covered with a tubing of flexible, substantially inert, impermeable material. No adhesive is needed to adhere the tubing to member 15 as the tubing, which has been placed over member 15 is locked on when the member 15 is attached to shaft 13. Member 15a is the leading edge to impart maximum strength to member 15. When member 15 is coated or covered with a tubing of flexible, substantially inert, impermeable material, member 15a as the narrower leading edge facilitates entry of member 15 between adjacent discs 12.

FIG. 4 is a cross section of rod-like member 15 having a coating 27 thereon of a flexible substantially inert, impermeable material which is able to withstand steam sterilization such as polyfluorinated hydrocarbon, e.g. Teflon. The properties of Teflon are summarized in the 1953 edition of Handbood of Material Trade Names, p. 558.

FIG. 5 is a cross section of another rod-like member 15 surrounded by tubing 28 of flexible, substantially inert, impermeable material which is able to withstand steam sterilization such as polyfluorinated hydrocarbon, e.g. Teflon.

Member 15 may also be used without any covering or tubing (not shown as obvious).

When used with a mutli-plate cell culture apparatus, the cell removing apparatus of the present invention is positioned initially against the inside wall of shell 10 by turning handle 14. When the cell culture operation is completed, the handle 14 is turned thereby rotating shaft 13 and causing rod-like member 15 to sweep in arcuate manner across the surface of disc 12 displacing cells it meets and pushing these cells off the edge of the disc into the liquid medium in the cell culture apparatus. The shaft 11 on which the disc is mounted is then partially rotated bringing another cell-coated portion of disc 12 within the area swept by member 15. About 3 partial rotations of shaft 11 are sufficient to enable member 15 to displace substantially all of the cells on disc 12. Member 15 may then be turned against the inner wall of shell 10 and raised or lowered to contact another disc. An alternate method is to insert the rod-like members into the disc and then turn the discs with the magnetic device.

What is claimed is:

1. Apparatus for removing cells from cell culture apparatus having a plurality of discs mounted on a central shaft, the cell removing apparatus comprising a substantially shaft-like member having mounted thereon substantially perpendicularly to the axis of the shaft-like member a plurality of spaced apart contacting members, each contacting member adapted to contact at least part of the surface of a disc, each contacting member having two arms, each arm attached separately to the shaft-like member, the arms being joined a distance removed from the shaft-like member whereby the contacting member is substantially triangular in shape having its base at about the shaft-like member and its apex a distance removed from the shaft-like member, and each contacting member being moved directly upon rotation of the shaft-like member.

2. Apparatus according to claim 1 wherein the portion of the shaft to which each arm is attached has two substantially flat surfaces, each surface provided with a recess.

3. Apparatus according to claim 2 wherein each arm is attached to a recess provided in one of the substantially flat surfaces.

4. Apparatus according to claim 3 wherein the recesses are at an angle with respect to one another.

5. Apparatus according to claim 4 wherein the recesses are substantially perpendicular with respect to one another.

6. Apparatus according to claim 1 wherein each arm is coated with a flexible, substantially inert, impermeable material.

7. Apparatus according to claim 1 wherein each arm is covered with a tubing of flexible, substantially inert, impermeable material.

8. Apparatus according to claim 7 wherein the tubing is polyfluorinated hydrocarbon.

9. A method of physically removing cells from a disc on which the cells have been cultured comprising the step of positioning a contacting member described in claim 1 on at least part of the surface of the disc and rotating the contacting member and the disc relative to each other.

10. In a multiplate propagator comprising a substantially cylindrical vessel having a plurality of spaced apart parallel discs on which discs cells are grown, the discs mounted on a rotatable shaft within the vessel, the improvement comprising a second shaft pivotably mounted within the cylindrical vessel, the second shaft having mounted thereon contacting means adapted to contact at least part of the surface of a disc upon pivotal movement of the second shaft whereby cells are removed from the surface of the disc, the contacting means comprising a cell contacting surface having means for laterally reinforcing the cell contacting surface.

11. A propagator according to claim 10 wherein the contacting means comprises a substantially wedge shaped member.

12. A propagator according to claim 11 wherein the wedge shaped member comprises two converging arms.

13. A propagator according to claim 12 wherein each arm is attached to a recess in the second shaft.

* * * * *